United States Patent [19]

Agee, Jr. et al.

[11] 3,990,003
[45] Nov. 2, 1976

[54] PULSED LOOP ANTENNA-CONDUIT ELECTROMAGNETIC RADIATOR TEST TECHNIQUE FOR ELECTROMAGNETIC SHIELDING FLAW DETECTION IN BURIED CONDUITS AND SHIELDED CONDUCTORS

[75] Inventors: Forrest J. Agee, Jr.; Huey A. Roberts, both of Alexandria, Va.

[73] Assignee: The United States of America as represented by the Secretary of the Army, Washington, D.C.

[22] Filed: Sept. 17, 1975

[21] Appl. No.: 614,712

[52] U.S. Cl. .................................. 324/52; 324/67
[51] Int. Cl.² ............................................. G01R 31/08
[58] Field of Search .............. 324/52, 66, 67, 3, 37; 340/40.5 R

[56] References Cited
UNITED STATES PATENTS

| | | | |
|---|---|---|---|
| 3,155,897 | 11/1964 | Rice | 324/52 |
| 3,315,155 | 4/1967 | Colani | 324/7 X |
| 3,418,207 | 12/1968 | Becker et al. | 324/52 X |
| 3,510,762 | 5/1970 | Leslie | 324/52 |
| 3,588,689 | 6/1971 | Crawford | 324/52 |
| 3,600,674 | 8/1971 | Roberts | 324/52 |
| 3,800,217 | 3/1974 | Lowrance | 324/52 X |
| 3,831,086 | 8/1974 | Pesto | 324/52 X |
| 3,836,842 | 9/1974 | Zimmermann et al. | 324/3 X |
| 3,878,453 | 4/1975 | Potter et al. | 324/67 X |

*Primary Examiner*—Gerard R. Strecker
*Attorney, Agent, or Firm*—Nathan Edelberg; Robert P. Gibson; Saul Elbaum

[57] ABSTRACT

A buried conduit shielding flaw detector is disclosed which provides a non-destructive method for testing buried pipes, cables and conduits to locate and measure shielding flaws without the necessity of excavation. A sense wire is longitudinally disposed within the pipe and a current amplitude measuring device is connected on one end thereof. A loop antenna external to the buried pipe, is moved along, parallel to the pipe being tested. The antenna is connected to a voltage pulsing means for generating a pulse of electromagnetic radiation which will couple the pipe. When the antenna is moved to within the vicinity of a flaw in the pipe, the electromagnetic radiation from the antenna is coupled through the flaw to the sense wire within the pipe. A current pulse is thereby induced in the sense wire which is, in turn, detected by the current amplitude measuring device. The amplitude of the induced current is characteristic of the size of the flaw detected in the pipe. When the current amplitude measuring device is an oscilloscope, the display of the induced current pulse has a signature which is characteristic of the type of flaw detected in the pipe. A second current amplitude measuring device may be coupled to the pipe itself so that the ratio of the magnitude of the current pulse induced in the sense wire, to a second current pulse induced in the pipe, can be determined independently of the distance separating the loop antenna from the pipe.

10 Claims, 8 Drawing Figures

LOOP CURRENT
(SINGLE LOOP)

500 nSec/div
150 Amps/div

SHIELD CURRENT 50 nsec/div
13.3 amps/div

SENSE WIRE CURRENT RUSTY JOINT FLAW 50 nsec/div
.67 mamps/div

SENSE WIRE CURRENT TRANSVERSE SLIT FLAW 50 nsec/div
.067 mamps

PULSED LOOP ANTENNA-CONDUIT ELECTROMAGNETIC RADIATOR TEST TECHNIQUE FOR ELECTROMAGNETIC SHIELDING FLAW DETECTION IN BURIED CONDUITS AND SHIELDED CONDUCTORS

RIGHTS OF THE GOVERNMENT

The invention described herein may be manufactured, used, and licensed by or for the United States Government for governmental purposes without the payment to us of any royalty thereon.

FIELD OF THE INVENTION

The invention disclosed generally relates to apparatus for detecting flaws in buried pipes and more particularly relates to apparatus employing electromagnetic radiation for the detection and characterization of flaws in buried pipes.

BACKGROUND OF THE INVENTION

Buried pipes and electrical cable shields are subject to environmental degradation due to corrosion, ground settling, thermal expansion, or excessive fluid pressure. The physical and hermetic integrity of buried pipes and cable shields is essential to properly carry out their intended function. A pipe which transmits fluids under pressure will constitute a substantial danger if the thickness of the pipe casing is reduced in localized regions through the agency of corrosion. The cylindrical shield for buried electrical cables will contribute to electrical power failures if the shield casing is cracked so as to admit ground water into it thereby shorting out the cables. The types of flaws which can contribute to the failure of a pipe or an electrical cable shield can be small by conventional standards, producing variations in the linear electrical resistance in the casing of only a milliohm or less. Conventional techniques for detecting flaws in buried conductive pipe casings and cable shields will not reveal the presence of such a flaw.

One prior art approach to detecting flaws in pipe casings is to energize electric wires within the pipe casing and to move a detector along the outside of the buried pipe, above the ground. The conductive property of the pipe casing strongly attenuates the electromagnetic radiation from the wires within the pipe so that a very weak signal is transmitted to the outside of the pipe. By virtue of the inverse square attenuation of the radiation from the outside of the pipe to the ground level location of the detector, the originally weak transmitted signal becomes virtually undetectable and variations in that signal indicative of flaws in the milliohm or less range becomes completely undetectable.

OBJECTS OF THE INVENTION

It is an object of the invention to provide a means for detecting flaws in a buried conductive pipe, in an improved manner.

It is another object of the invention to measure the size of the flaw in a buried conductive pipe, in an improved manner.

It is still another object of the invention to characterize the type of flaw detected in a buried conductive pipe.

It is still a further object of the invention to measure the flaw in a buried conductive pipe substantially independent of the depth at which the pipe is buried.

SUMMARY OF THE INVENTION

These and other objects, features, and advantages of the invention are accomplished by the buried conduit shielding flaw detector disclosed herein. The buried conduit shielding flaw detector comprises a sense wire longitudinally disposed within the buried pipe. A current amplitude measuring device is connected to one end of the sense wire. A loop antenna, external to the pipe, is moved along the axis of the pipe with the plane of the loop positioned substantially parallel to the axis of the pipe. A voltage pulse means is connected to the antenna for generating a pulse of electromagnetic radiation coupling the pipe. When the antenna comes within the vicinity of a flaw in the pipe casing, the electromagnetic radiation will couple the sense wire through the flaw in the pipe thereby inducing a current pulse in the sense wire. This induced current pulse is detected by the measuring device, thereby indicating the location of a flaw in the pipe casing. The magnitude of the induced current pulse is characteristic of the size of the flaw detected in the pipe. If the current amplitude measuring device is an oscilloscope, the current pulse displays a signature characteristic of the type of the flaw detected in the pipe. A second current amplitude measuring device may be coupled to the pipe casing itself. This enables the ratio of the magnitude of the current pulse induced in the sense wire to the current pulse induced in the pipe to be determined independently of the distance separating the loop antenna from the pipe.

DESCRIPTION OF THE FIGURES

The above and further objects and novel features of the invention will more fully appear from the following description when the same is read in connection with the accompanying drawings. It is to be understood, however, that the drawings are for the purpose of illustration only, and are not intended as a definition of the limits of the invention.

FIG. 2b illustrates the current pulse produced by a 42kv pulser driving the antenna of FIG. 2a.

FIG. 4b illustrates the relative positions of the loop and transverse split in the pipe casing, employed in the generation of the graph of FIG. 4a.

DISCUSSION OF THE PREFERRED EMBODIMENT

Figure 1:
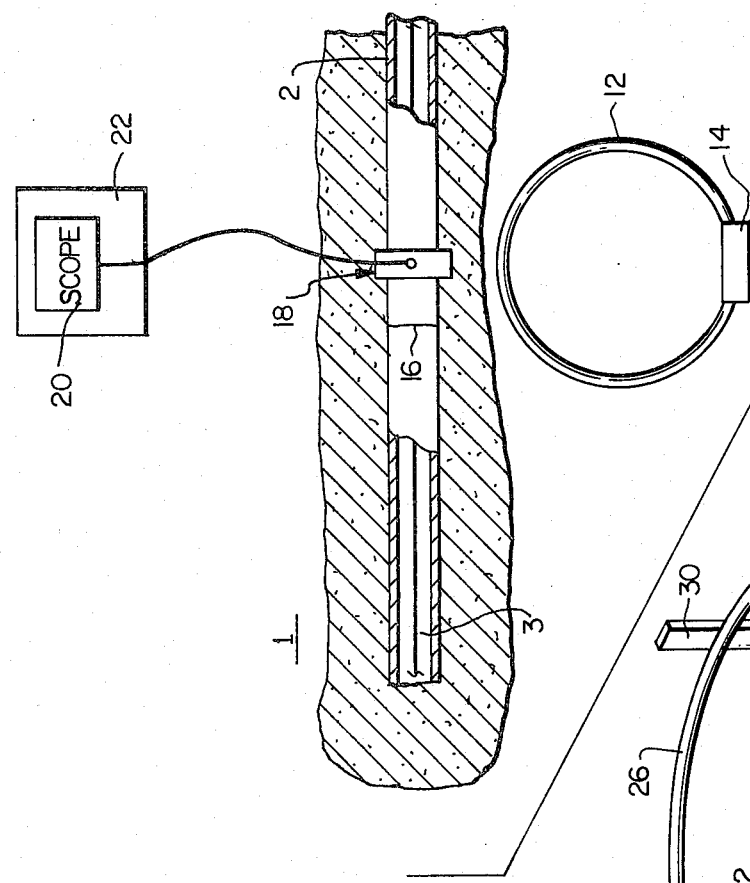
FIG. 1 illustrates a cross sectional, plan view showing the relative arrangement of the elements of the invention when testing for flaws in a buried pipe.

FIG. 1 shows the general relationship of the elements of the invention as they are employed in the detection of flaws in a buried pipe casing. A cross sectional view in the ground 1 shows the shield or pipe casing 2 buried therein. The sense wire 4 is longitudinally disposed within the shield 2 and is electrically insulated from the pipe casing. The distant end 3 may be open, shorted to ground, terminated in any impedance, or it may be terminated with a resistive load to match its impedance. The pipe casing and sense wire may be of any length to the distant end. The sense wire 4 may, in fact, be the in situ electric cable in a cable shield 2. The sense wire 4 may, in fact, be the in situ power or electronic cable in an electrical conduit. The sense wire 4 is connected by means of the current probe 6 and the wire 8 to the current amplitude measuring device 10. The current amplitude measuring device 10 may be an oscilloscope, or other suitable current amplitude measuring device. The sense wire 4 can extend beyond the measurement point and a clamp around current probe 6 can be used to measure the current without disturbing the sense wire 4 as in the case of a wire routed through a manhole 24.

Located above the ground level 1 is the loop antenna 12 which is driven by the voltage pulsing means 14. The voltage pulsing means connected to the antenna 12, generates a pulse of electromagnetic radiation which will be transmitted through the ground 1 to couple the casing of the shield 2. When the loop antenna 12, which is positioned substantially parallel to the axis of the shield 2, is moved axially along the length of the shield 2 to come within the vicinity of the flaw 16 in the casing shield 2, electromagnetic radiation from the antenna 12 will couple the sense wire 4 through the flaw 16, thereby inducing a current pulse in the sense wire 4. This current pulse is in turn detected by the measuring device 10. In this manner, the location of the flaw 16 in the shield 2 may be determined.

The antenna loop 12, which, in its preferred embodiment, is 9 feet in diameter, couples the maximum current into the buried shield 2, when it is horizontally displaced from the axis of the shield 2 by a distance of from 4 ½ feet to 10 feet, depending upon the depth of burial of the shield 2. Tests at depths of burial of from 3 feet to over 14 feet indicate that the displacement is not critical, as long as the loop 12 is not directly over the buried shield 2 to be tested. When the antenna 12 is directly over the shield 2, a null in the current induced in the shield, occurs.

In using the loop 12 to test a buried shield 2, the operator merely moves the loop along the axial direction of the shield 2 while observing the current amplitude measuring device 10 for an indication of current on the sense wire 4. As the pulsed antenna loop 12 approaches a flaw 16, current pulses appear on the sense wire 4. These current pulses grow to an amplitude maximum when the loop 12 is opposite the flaw 16, and then subside as the loop goes past the flaw 16. In this fashion, it is possible to locate a flaw so as to enable subsequent excavation at the appropriate point to repair the shield 2, if required.

It is a basic physical principle that the intensity of the electromagnetic radiation radiated from a source is reduced by the inverse square of the distance from the source and furthermore, that electromagnetic radiation absorbtive materials located in the vicinity of the radiating source will further reduce the magnitude of the intensity of the radiation transmitted therethrough. The effect of the depth of burial of the shield 2 in the ground 1 can be minimized, within limits, by measuring the ratio of the current induced in the sense wire 4 to the current induced in the casing of the shield 2, itself. This is done, as shown in FIG. 1, by positioning a current probe 18 around the shield 2, and connecting the probe 18 to the second current amplitude measuring device 20, which may be an oscilloscope or other suitable measuring instrument. When the antenna 12 is positioned in the vicinity of a flaw 16, the ratio of $I_{sw}$, the current induced in the sense wire 4 to $I_c$, the current induced in the casing of the shield 2, will remain substantially invarient over a limited range of depths for burial of the shield 2.

This technique of coupling the electromagnetic radiation through a flaw to the sense wire can be employed to characterize various types of flaws by the signature which they produce upon the oscilloscope 10. A brief reference to FIG. 3b illustrates the signature of the sense wire current induced by a rusty joint flaw and FIG. 3c illustrates the signature of the sense wire current induced by a transverse slit flaw. Other aperture flaws, as for example longitudinal cracks or slots, may be characterized by FIG. 3c and other resistive joint type flaws, for example loose or rusted couplings or unions, can be characterized by the signature of FIG. 3b. This identification can be useful in predicting the seriousness of a flaw.

Figure 2A:
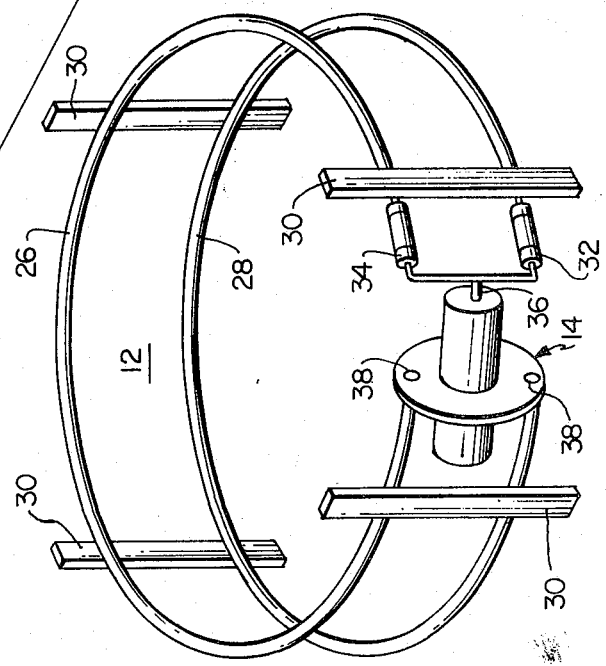
FIG. 2a illustrates the loop antenna.

FIG. 2a illustrates the loop antenna 12 as it is coupled to the voltage pulsing means 14. In the particular illustration of FIG. 2a, a double loop antenna is comprised of a first substantially circular loop 26 and the second substantially circular loop 28 mounted on the insulated separators 30. Loop 26 is connected to a 40 ohm resistor 34 and loop 28 is connected to a 40 ohm resistor 32. Resistors 32 and 34 are connected in common to a first terminal 36 of the 42kv pulser 14. The second end of the loops 26 and 28 are connected to a second terminal 38 of the pulser 14. The diameter of the loops 26 and 28 is approximately 9 feet.

Figure 2B:
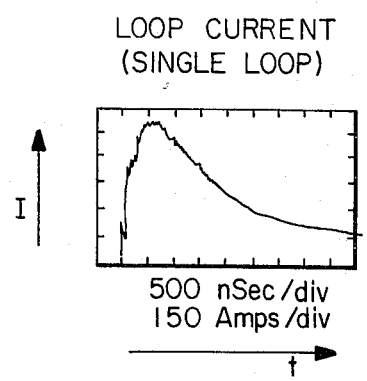

FIG. 2b illustrates the current characteristics of the pulser and antenna combination of FIG. 2a. It is seen that the pulser 14 drives the loops 26 and 28 so as to achieve a current pulse having a rise time of approximately 750 Amperes in 500 nanoseconds. This large time rate of change of current generates a substantial electromagnetic wave which radiates out from the antenna 12.

Figure 3A:
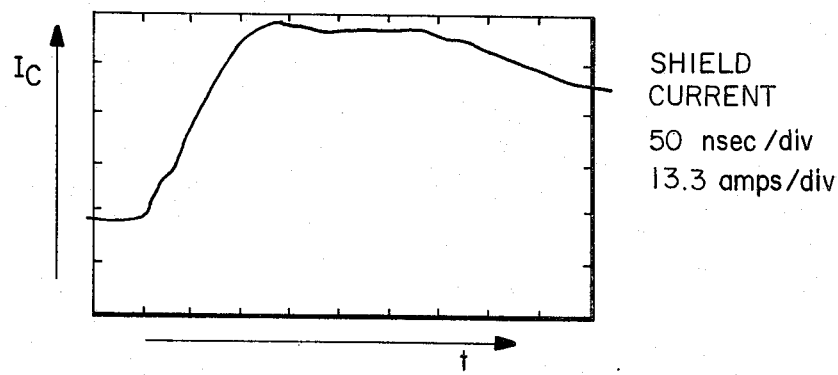
FIG. 3a is a graph of the current induced in the shield casing in FIG. 1 by a 40kv loop pulser.
Figure 3B:
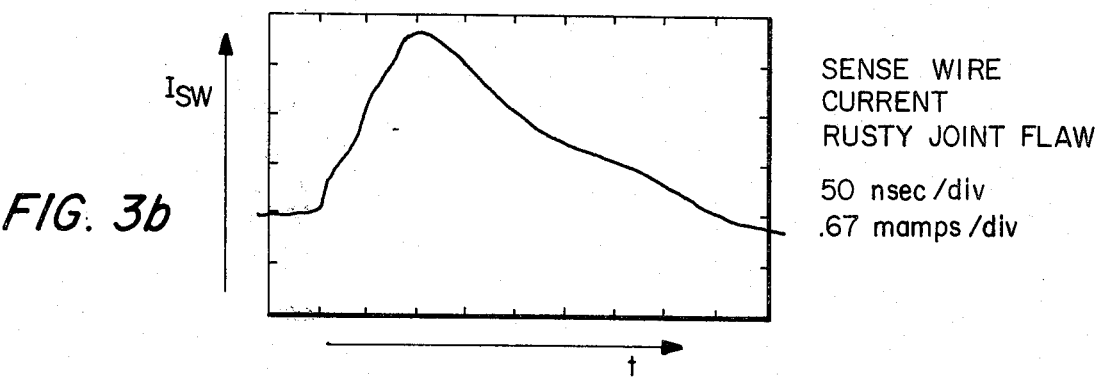
FIG. 3b is a graph of the current induced in the sense wire of FIG. 1 for a 40kv loop pulser, where the flaw is that of a rusty joint.
Figure 3C:
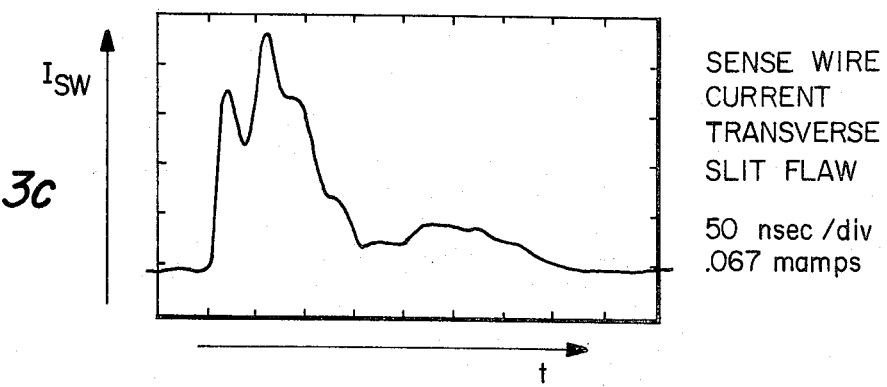
FIG. 3c is a graph of the current induced in the sense wire of FIG. 1 using a 40kv loop pulser, where the flaw is a transverse split in the casing.

Typical currents induced in the shield 2 for the antenna configuration of FIG. 2a is shown in FIG. 3a. Correspondingly, a typical sense wire current induced in the sense wire 4 for a rusty joint flaw is shown in FIG. 3b and a typical sense wire current for a transverse split flaw is shown in FIG. 3c.

Figure 4A:
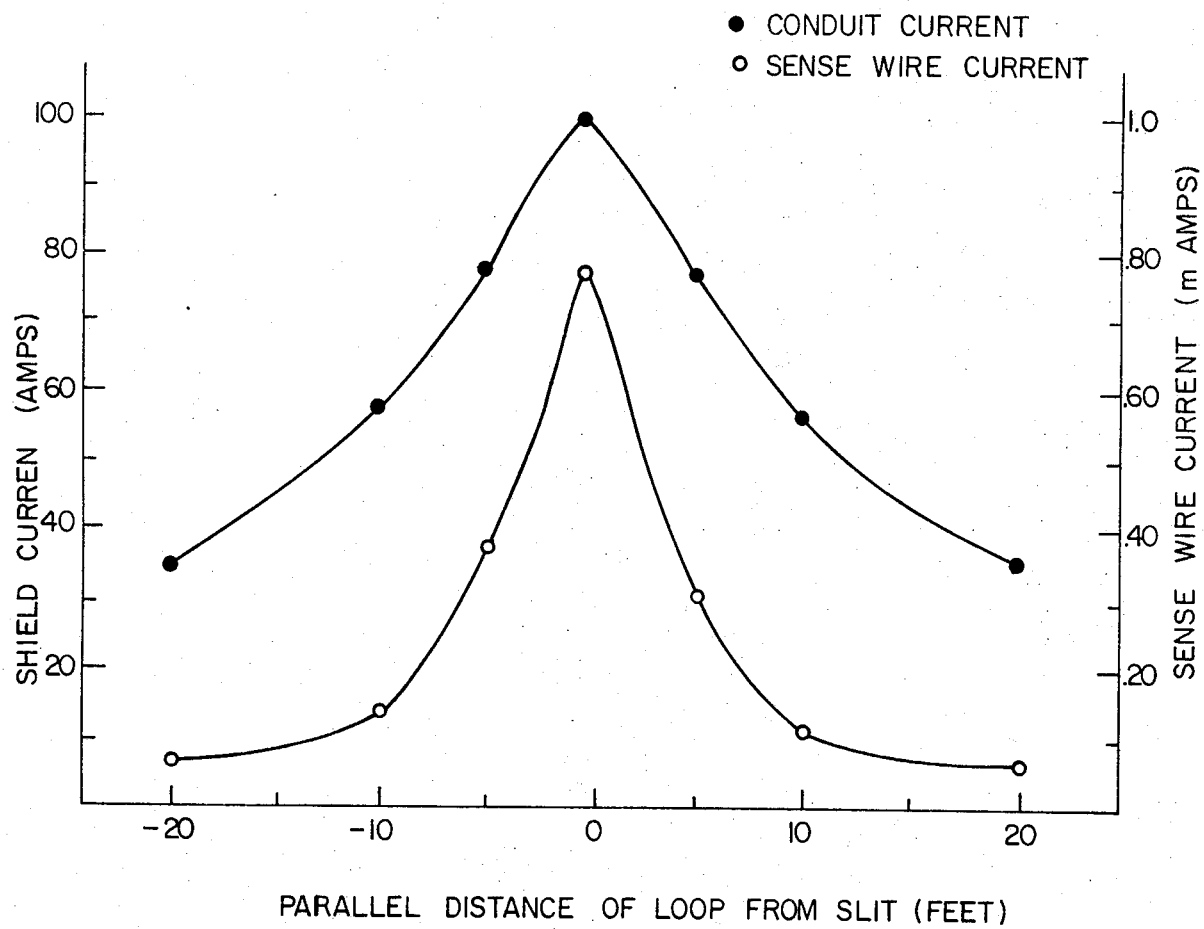
FIG. 4a is a graph of the magnitude of the shield current and the sense wire current as a function of the axial displacement of the loop antenna from a transverse split flaw in the pipe casing.
Figure 4B:
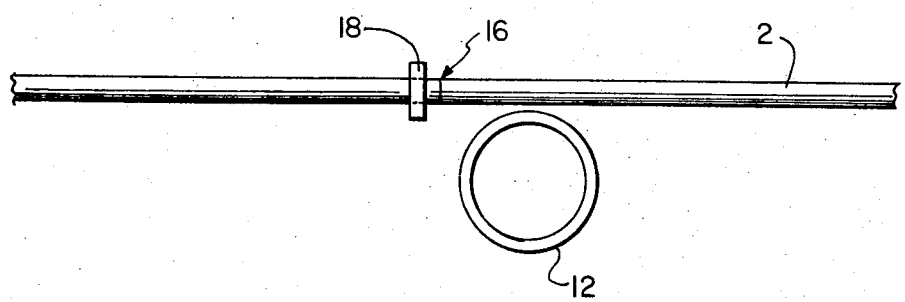

FIG. 4a shows a graph of the sense wire current as a function of the axial displacement of the center of the loop antenna 12 with respect to the location of the transverse slit 16 in the shield 2, as shown in FIG. 4b. It is to be noted that there is substantial definition in the determination of the location of the transverse slit 16 in the buried shield 2. The graph of FIG. 4a is taken from experiment with a 100kv loop pulser.

Although only one embodiment of the invention has been illustrated in the accompanying drawings and described in the foregoing specification, it should be understood by those skilled in the art that various changes such as in the relative dimensions of the parts, number of antennas, materials used, and the like, as well as the suggested manner of the use of the apparatus of the invention, may be made therein without departing from the spirit and scope of the invention.

We claim:

1. Apparatus for detecting flaws in a buried conductive pipe, comprising:
   a sense wire longitudinally disposed within said pipe;
   a current amplitude measuring device coupled to said sense wire;
   a loop antenna external to said pipe, with the plane of said loop positioned substantially parallel to the axis of said pipe;
   a voltage pulsing means connected to said antenna, for generating a pulse of electromagnetic radiation coupling said pipe;
   said electromagnetic radiation coupling said sense wire through a flaw in said pipe, thereby inducing a current pulse in said sense wire which is detected by said measuring device;
   whereby the location of a fault in said pipe may be determined.

2. The apparatus of claim 1, wherein said current amplitude measuring device further comprises:
   a current probe attached to said sense wire;
   an oscilloscope having an input connected to said current probe.

3. The apparatus of claim 1, wherein said loop antenna further comprises:
   a substantially circular, open loop of wire;
   a resistor connected to a first end of said loop;
   said voltage pulsing means having a first terminal connected to said resistor and a second terminal connected to a second end of said loop.

4. The apparatus of claim 1, wherein said loop antenna further comprises:
   a first substantially circular, open loop of wire;
   a second substantially circular, open loop of wire, coaxial with but axially displaced from said first loop;
   a first resistor connected to a first end of said first loop;
   a second resistor connected to a first end of said second loop;
   said voltage pulsing means having a first terminal connected to said first resistor and said second resistor and a second terminal connected to a second end of said first loop and a second end of said second loop.

5. The apparatus of claim 4, wherein said loop antenna further comprises:
   said first and second loops having a diameter of approximately 9 feet;
   said first resistor having a resistance of approximately 40 ohms;
   said second resistor having a resistance of approximately 40 ohms;
   said voltage pulsing means being a 40 kilovolt pulser for driving said first and second loops to achieve a current pulse having a rise time of approximately 750 Amperes in 500 nanoseconds.

6. The apparatus of claim 4, wherein said voltage pulsing means drives said first and second loops to achieve a current pulse having a rise time of approximately 750 Amperes in 500 nanoseconds.

7. The apparatus of claim 1, which further comprises:
   a second current amplitude measuring device coupled to said pipe;
   whereby the ratio of the magnitude of said current pulse induced in said sense wire to a second current pulse induced in said pipe can be determined independently of the distance separating said loop antenna from said pipe.

8. The apparatus of claim 1, wherein:
   said pipe is the shielding for an electrical cable; and
   said sense wire is the electrical cable contained within said shield.

9. The apparatus of claim 2, wherein:
   said oscilloscope displays said current pulse as a signature characteristic of the type of flaw detected in said pipe.

10. The apparatus of claim 1, wherein:
    said current pulse measured by said measuring device has an amplitude characteristic of the size of flaw detected in said pipe.

* * * * *